United States Patent [19]
McBride

[11] Patent Number: 6,051,218
[45] Date of Patent: *Apr. 18, 2000

[54] TUMOR RADIOSENSITIZATION USING GENE THERAPY

[75] Inventor: William H. McBride, Los Angeles, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/597,524

[22] Filed: Feb. 2, 1996

[51] Int. Cl.$^7$ .................................................. A61K 48/00

[52] U.S. Cl. ........................ 424/93.21; 514/44; 435/375

[58] Field of Search ............................. 435/320.1, 240.2, 435/6, 172.3, 7.2, 375; 935/62, 52, 55–57, 34, 70, 71, 33, 65; 424/93.1, 93.21, 184.1, 9.4; 514/44

[56] References Cited

U.S. PATENT DOCUMENTS 5,399,346   3/1995   Anderson et al. ................... 424/93.21

OTHER PUBLICATIONS

Malcolm S. Mitchell, *Combining Chemotherapy and Biomodulation in the Treatment of Cancer, in Human Tumor Antigens and Specific Tumor Therapy*, UCLA Symposium at Keystone Colorado 99:345–358 (Metzgar and Mitchell ed., 1989).

Vieweg et al. "Immunotherapy of Prostate Cancer in the Dunning Rat Model: Use of Cytokine Gene Modofied Tumor Vaccines," Cancer Research, vol. 54: 1760–1765., Apr. 1,1994.

Vieweg et al. "Considerations for the use of Cytokine–Secreting Tumor Cell Preparations for Cancer Treatment," Cancer Investigation, vol. 13: 193–201, 1995.

Colombo, et al., "Granulocyte Colony–stimulating a Factor Gene Transfer Suppresses Tumorigenicity of a Murine Adenocarcinoma In Vivo." *J. Exp. Med.* 173:889–897 (1991).

Golumbek et al., "Controlled Release, Biodegradable Cytokine Depots: A New Approach in Cancer Vaccine Design." *Cancer Research* 53:5841–5844 (1993).

Lange et al., "A Pilot Study of the Combination of Interleukin–2–Based Immunotherapy and Radiation Therapy." *Journal of Immunotherapy* 12:265–271 (1992).

Matsumoto et al., "Recombinant Human Granulocyte Colony–Stimulating Factor Inhibits the Metastasis of Hematogenous and Non–Hematogenous Tumors in Mice." *Int. J. Cancer* 49:444–449 (1991).

McBride et al., "Modification of Tumor Microenvironment by Cytokine Gene Transfer." *Acta Oncologica* 34:447–451 (1995).

McBride and Dougherty, "Radiotherapy for genes that cause cancer." *Nature Medicine* 1:1215–1217 (1995).

McDonald et al., "Combined Betaseron R (Recombinant Human Interferon Beta) and Radiation for Inoperable Non––Small Cell Lung Cancer." *Int. J. Radiation Oncology Biol. Phys.* 27:613–619 (1993).

Sersa et al., "Anti–Tumor Effects of Tumor Necrosis Factor Alone or Combined with Radiotherapy." *Int. J. Cancer* 42:129–134 (1988).

Younes et al., "Radiation–Induced Effects on Murine Kidney Tumor Cells: Role in the Interaction of Local Irradiation and Immunotherapy." *The Journal of Urology* 153:2029–2033 (1995).

Coghlan, A. "Gene dream fades away," New Scientist, vol. 145: 14–15, Nov. 25, 1995.

Brown, D. "Gene Therapy 'Oversold' by Researchers, Journalists," The Washington Post, A22, Dec. 8, 1995.

Gansbacher, et al. "Retroviral Vector–Mediated Cytokine–Gene Transfer into Tumor Cells," Cancer Investigation, vol. 11(3):345–354, Mar. 1993.

McBride et al. "Interleukin–3 in Gene Therapy of Cancer," Filia Biologica, vol. 40: 62–73, Feb. 1994.

Zhang et al. "Gene Therapy strategies for cancer," Expert Opinion on Investigational Drugs, vol. 4(6): 487–514, Jun. 1995.

Weichselbaum et al. "Gene Therapy Targeted by Radiation Preferentially Radiosensitizes Tumor Cells," Cancer Research, vol. 54: 4266–4269, Aug. 15, 1994.

Dranoff, et al. "Vaccination with irradiated tumor cells engineered to secrete murine granulocyte–macrophage colony–stimulating factor stimulates potent, specific, and long–lasting anti–tumor immunity," Proc. Natl. Acad. Sci., vol. 90:3539–3543, Apr. 1993.

Patchen et al. "Mast cell growth factor (C–kit ligand) in combination with granulocyte macrophage colony–stimulating factor and interleukin–3: in vivo hemopoietic effects in irradiated mic compared to in vitro effects," Biotherapy, vol. 7(1): 13–26, Jan. 1994.

Tepper et al. "Experimental and Clinical Studies of Cytokine Gene–Modified Tumor Cells," Human Gene Therapy, vol. 5: 153–164, 1994.

*Primary Examiner*—Karen M. Hauda
*Attorney, Agent, or Firm*—Campbell & Flores LLP

[57] ABSTRACT

The invention provides a method of radiosensitizing a tumor in a subject by contacting the tumor with a cytokine or a nucleic acid molecule encoding a cytokine. The invention also provides a method of radiosensitizing a tumor in a subject by administering, at a site other than the tumor, a cell genetically modified to express a cytokine. The invention further provides a method of reducing the severity of a cancer in a subject by administering a cytokine at the site of the tumor or by immunizing the subject at a site other than the tumor with tumor cells genetically modified to express a cytokine, and treating the tumor with radiotherapy.

2 Claims, No Drawings

TUMOR RADIOSENSITIZATION USING GENE THERAPY

BACKGROUND OF THE INVENTION

1. Field of the Invention

The present invention relates generally to cancer therapy and, more particularly, to compositions and methods for sensitizing a cancer in a subject to radiation therapy.

2. Background Information

Improved methods and novel agents for treating cancer have resulted in increased survival time and survival rate for patients with various types of cancer. For example, improved surgical and radiotherapeutic procedures result in more effective removal of localized tumors. Surgical methods, however, can be limited due, for example, to the location of a tumor or to dissemination of metastatic tumor cells. Radiotherapy also can be limited by these factors, which limits the dose that can be administered. Tumors that are relatively radioresistant will not be cured at such a dose.

Immunotherapeutic methods also are being examined as a means to treat a cancer by stimulating the patient's immune response against the cancer. In particular, the role of cytokines, which are cellular factors that can modulate an immune response, is an important factor to consider when planning an immunotherapeutic procedure. For example, expression of a cytokine such as interleukin-2 (IL-2) can increase the proliferation of T cells, which are involved in the cellular immune response against a cancer.

It is well known, however, that cytokine administration frequently is associated with toxic effects that limit the therapeutic value of these agents. For example, severe hypotension and edema limit the dose and efficacy of intravenous and intralymphatic IL-2 administration. In addition, flu-like symptoms or fatigue often are associated with the administration of various cytokines. The toxicity of systemically administered lymphokines is not surprising as these agents mediate local cellular interactions and normally are secreted only in very small quantities.

To circumvent the toxicity of systemic cytokine administration, an alternative approach involving cytokine gene transfer into tumor cells has produced anti-tumor immune responses in several animal tumor models. In these studies, the expression of cytokines following cytokine gene transfer into tumor cells resulted in a reduction in tumorigenicity of the cytokine-secreting tumor cells when implanted into syngeneic hosts. Reduction in tumorigenicity has been reported in studies using, for example, IL-2, interferon-γ or interleukin-4. In addition, the treated animals often developed systemic anti-tumor immunity and were protected against subsequent tumor cell challenges with unmodified tumor cells.

Although a single treatment modality such as radiation therapy, chemotherapy, surgery or immunotherapy can result in improvement of a patient, superior results can be achieved when such modalities are used in combination. In particular, treatment with a combination of radiotherapy, which can be directed to a localized area containing a tumor, and chemotherapy or immunotherapy, which provide a systemic mode of treatment, can be useful where dissemination of the disease has occurred or is likely to occur. Unfortunately, the therapeutic usefulness of radiation therapy can be limited where the tumor cells are relatively radioresistant, since the does is limited by the tolerance of normal tissue in the radiation field. Thus, there exists a need to sensitize cancer tumors to the effects of radiotherapy so that it can more effectively reduce the severity of a tumor in a patient. The present invention satisfies this need and provides related advantages as well.

SUMMARY OF THE INVENTION

The invention provides a method of radiosensitizing a tumor in a subject by contacting the tumor with a cytokine such as interleukin-3 or granulocyte-macrophage colony stimulating factor or granulocyte colony stimulating factor. For example, the invention provides a method of radiosensitizing a tumor in a subject by contacting the tumor with interleukin-3. As an additional advantage, a method of the invention provides an enhanced systemic immune response in the subject against the cancer.

The invention also provides a method of radiosensitizing a tumor in a subject by administering, at a site other than the tumor, an immunizing composition containing a cytokine and a tumor antigen. For example, the invention provides a method of radiosensitizing a tumor in a subject by administering, at a site other than the tumor, tumor cells that have been genetically modified to express a cytokine.

The invention further provides a method of reducing the severity of a cancer in a subject by immunizing the subject, at a site other than the site of the tumor, with tumor cells genetically modified to express a cytokine express and secrete a cytokine, then administering a radiotherapeutic dose of radiation.

DETAILED DESCRIPTION OF THE INVENTION

The present invention provides a method of radiosensitizing a tumor in a subject by contacting the tumor with a cytokine such as interleukin-3 (IL-3), granulocyte-macrophage colony stimulating factor (GM-CSF) or granulocyte colony stimulating factor (G-CSF). As used herein, the term "contacting," when used in reference to a cytokine and a tumor, means that the cytokine is present in the location of the tumor, particularly in the location of a localized tumor. As disclosed herein, a tumor can be contacted with a cytokine, for example, by injecting a solution containing the cytokine into the region of the tumor, by administering a nucleic acid molecule encoding a cytokine into the region of the tumor, wherein the nucleic acid molecule is taken up by cells in the tumor such that the cytokine is expressed, or by administering a cell that has been genetically modified to express (and secrete) the cytokine into the region of a tumor.

Since an additional advantage of a method of the invention is that a systemic immune response against the cancer occurs in the subject, a composition containing a cytokine or a nucleic acid molecule encoding a cytokine is referred to herein generally as an "immunizing composition." In addition, the term "immunizing" is used generally to refer to the administration of such an immunizing composition to a subject.

The invention also provides a method of radiosensitizing a tumor in a subject by administering, at a site other than the tumor, an immunizing composition comprising a cell genetically modified to express a cytokine. For example, the invention provides a method of radiosensitizing a tumor in a subject by administering to the subject an immunizing composition comprising tumor cells genetically modified to express a cytokine. Such an immunizing composition can be administered at the site of the tumor, in which case the cytokine is IL-3 or GM-CSF or G-CSF, or can be administered at a site other than the tumor site, in which case the cytokine can be an interleukin, an interferon, a tumor necrosis factor or a colony stimulating factor, and preferably is IL-3 or GM-CSF or G-CSF.

In one embodiment of the invention, an immunizing composition, which contains a cytokine such as IL-3 or GM-CSF or G-CSF, is administered at the site of a tumor in a subject. As a result, the microenvironment of the tumor is altered such that a systemic immune response against the tumor in the tumor occurs in the subject and the tumor is radiosensitized.

In another embodiment of the invention, an immunizing composition, which contains a cytokine and a tumor antigen, is administered at a site other than the tumor site in the subject. As a result of the administration of the immunizing composition at a site other than a tumor site, a systemic immune response is stimulated in the subject and the tumor can become radiosensitized.

An immunizing composition, which contains a cytokine or a nucleic acid molecule encoding a cytokine, can be administered to a subject having a cancer. As a result, an immune response is stimulated in the subject against the cancer, wherein the systemic immune response or alterations induced by the immune response in the tumor microenvironment can radiosensitize the subject's cancer. Subsequent radiotherapy then can be used to treat the radiosensitized tumor and the systemic immune response can destroy remaining tumor cells, including any metastatic lesions. Thus, in another embodiment, the invention provides a method of reducing the severity of a cancer in a subject, comprising immunizing the subject with an immunizing composition and administering a dose of radiation to the site of the cancer.

As disclosed herein, immunization of a subject provides a means to radiosensitize a tumor such that it can be treated more effectively by radiotherapy (see Example I). As used herein, the term "tumor" means a localized growth of cancer cells, which can be the site where a cancer originally formed or can be a metastatic lesion. The terms "tumor cell" and "cancer cell" are used interchangeably herein to mean a malignant cell.

A method of the invention is particularly useful for treating a subject having metastatic lesions that have disseminated from an original tumor site because, in addition to radiosensitizing the tumor, a method of the invention also provides a systemic immune response, which can kill disseminated cancer cells. Thus, the invention is useful for treating a subject with a cancer such as a melanoma or any other cancer in which the dissemination of metastatic lesions is common, and provides the additional advantage that recurrence of a tumor is less likely to occur following treatment.

A method of the invention radiosensitizes a tumor in a subject. As used herein, the term "radiosensitize," when used in reference to a tumor or a tumor cell, means to increase susceptibility of the tumor or tumor cell to the effects of radiation. It is recognized that the term "radiosensitize" is used in a comparative sense and, with regard to the present invention, indicates that the radiation dose to reduce the severity of a cancer in a subject that has been immunized as disclosed herein is less than the radiation dose that would have been required if the subject had not been immunized. In contrast, the term "radioresistant" means that a cell is relatively refractory to the effects of radiation.

As used herein, the term "effects of radiation" refers to the well known cytostatic and cytotoxic effects that radiation has on a cell. For example, exposure of a cell to radiation can inhibit progression of the cell through the cell cycle; can damage nucleic acids, proteins, or other macromolecules in a cell; or can kill the cell by inducing apoptosis. It should be recognized that these effects of radiation are interrelated and represent a continuum of effects, the magnitude of which is dependent, in part, on the radiation dose and on the relative radiosensitivity of the target cell.

The present invention provides a means to radiosensitize a tumor in a subject, such that the tumor is more susceptible the effects of radiation, including tumor cell killing. For convenience, reference is made generally herein to tumor cell "killing." It should be recognized, however, that an increased susceptibility of a tumor cell to any of the effects of radiation can provide a significant therapeutic advantage to a cancer patient.

The effectiveness of a method of the invention in treating a subject can be identified using well known methods. For example, the effectiveness of treatment can be identified by detecting, in a subject immunized as disclosed herein, prolonged survival of the subject, disappearance of the tumor, or a decreased rate of growth of an irradiated tumor as compared to the rate of growth prior to irradiation. In human cancer patients, such measurements generally are made using well known imaging methods such as magnetic resonance imaging, computerized axial tomography and X-rays. In addition, determination of the level of a tumor marker such as the detection of levels of circulating carcinoembryonic antigen (CEA) or prostate specific antigen or the like also can be used as an indication of the effectiveness of a treatment. Thus, the effectiveness of a method of the invention can be determined by measuring a decrease in the growth rate of a tumor or an appropriate change in the level of a circulating marker, the presence or relative level of which is indicative of cancer.

Radiation therapy is a conventional method for treating cancer. In particular, radiotherapy is useful in cases where the tumor is relatively localized and not excessively large, or where surgical excision of the tumor is contraindicated due, for example, to the location of the tumor. Radiation therapy is a preferred method of treating, for example, prostate cancer and brain tumors. The skilled artisan would know the appropriate dosages, treatment schedules and radiation sources to use for treating a particular cancer.

Various factors can limit the usefulness of radiotherapy. Ultimately, however, the success of radiotherapy is limited due to unacceptable patient morbidity that occurs as a result of consequent irradiation of normal tissue in the radiation field. In particular, exposure of rapidly renewing tissues, including, bone marrow, small intestine and skin, to radiation can lead to unacceptable patient morbidity. However, slowly proliferating tissues, including nervous tissue, also can be damaged irreversibly if exposed to an excessively high dose of radiation.

Administration of radiotherapy as fractionated doses over a period of time can provide advantages over administration of a single large dose. In particular, fractionated doses of radiation are useful if the cells in the normal tissue in the radiation field can repair radiation induced damage faster or more efficiently than the tumor cells in the radiation field. In this case, fractionated doses can be administered at intervals that preferentially allow repair of the normal cells as compared to the tumor cells. In addition, tumors generally have relatively hypoxic regions that are less susceptible to radiation damage. Fractionated radiation doses also can permit reoxygenation to occur in such regions, due to sloughing off of tumor cells killed by previous doses, thus improving the effectiveness of subsequent radiation doses.

Considerable research has been directed to the identification of chemical agents that selectively increase the radiosensitivity of tumor cells, but not of normal cells. Such radiosensitizers can work, for example, by effecting reoxygenation of a hypoxic region of a tumor or by acting as an oxygen mimetic. Since normal tissue is well oxygenated, such a radiosensitizer can increase the sensitivity of the tumor cells, while having relatively less effect on the normal cells, thus effectively radiosensitizing the cancer cells.

Cytokines are a class of molecules that, in some cases, also can act as radiosensitizing agents. Cytokines constitute a family of polypeptides that are produced by leukocytes and other cells and regulate the immune and inflammatory responses in humans (Thomson, *The Cytokine Handbook* (Academic Press; 1994), which is incorporated herein by reference; see Chap. 1). Cytokines are polypeptides or glycoproteins, including the heterodimeric IL-12, that bind to high affinity cell surface receptors. Numerous cytokines, including interleukins 1-13 (IL-1, IL-2, IL-3, etc.), interferons $\alpha$, $\beta$ and $\gamma$ (Ifn-$\alpha$, Ifn-$\beta$ and Ifn-$\gamma$), tumor necrosis factors $\alpha$ and $\beta$ (TNF-$\alpha$ and TNF-$\beta$), colony stimulating factors such as macrophage colony stimulating factor (M-CSF), G-CSF and GM-CSF, and transforming growth factor $\beta$ (TGF$\beta$) and stem cell factor, are known in the art (Thomson, supra, 1994).

Cytokines can increase or decrease the rate of cell proliferation and can affect the differentiation state of a target cell, including cells involved in the immune response. For example, IL-2, IL-4 and IL-7 are T cell growth factors, which increase proliferation of T cells; M-CSF, GM-CSF, G-CSF and IL-3 can induce bone marrow cells to differentiate into macrophages or granulocytes or both; and Ifn-$\gamma$, IL-4, IL-7 and GM-CSF can activate macrophages, increasing their tumoricidal activity.

In addition, the expression of specific combinations of cytokines can be particularly useful for stimulating an immune response. For example, expression of IL-1, IL-6 or a TNF can enhance IL-2 induced T cell proliferation; IL-6 can enhance IL-4 induced T cell proliferation; and of Ifn-$\gamma$, IL-2 and IL-12 can stimulate T cells of the T helper-1 class, which are involved in the cellular immune response. Thus, it can be particularly useful to express specific combinations of cytokines for the purpose of stimulating an immune response.

It is recognized, however, that the expression of other combinations of cytokines can inhibit an immune response. For example, TGF-$\beta$ can inhibit IL-2 action and IL-10 can inhibit cytokine production and antigen-specific proliferation of T helper-1 cells. In addition, various types of cancer cells can express receptors for a cytokine such as IL-2 or IL-1, such that expression of the cytokine can induce proliferation of the tumor cells. Thus, the selection of a cytokine or combination of cytokines to be administered to a subject must be considered carefully (Thomson, supra, 1989; see Chap. 25).

In some cases, cytokines can act to radiosensitize cancer cells. For example, tumor cells genetically modified to express IL-6 or IL-7 were more sensitive to radiation induced killing in vitro than were the corresponding unmodified tumor cells (McBride et al., *Acta Oncol.* 34:447–451 (1995), which is incorporated herein by reference). Surprisingly, however, when unmodified tumor cells or IL-7 expressing tumor cells were injected into a mouse thigh, then treated with radiotherapy, the IL-7 expressing tumor cells were more radioresistant than the unmodified tumor cells.

In other studies, human tumor cells that were genetically modified to express TNF-$\alpha$ when irradiated, then xenografted into nude mice, were more sensitive to radiation therapy than were the corresponding unmodified tumor cells (Weichselbaum et al., *Canc. Res.* 54:4266–4269 (1994); Hallahan et al., *Nat. Med.* 1:786–791 (1995), each of which is incorporated herein by reference). TNF-$\alpha$ also can act as a radioprotector, however, decreasing, for example, the lethal effect of radiation in mice (Neta et al., *J. Exp. Med.* 175:689–694 (1992)). IL-1 also has been described as providing a radioprotective effect (Neta et al., supra, 1992), although studies using another system found no such radioprotective effect for IL-1, or for IL-2 or IL-3 (Gallicchio et al., *J. Biol. Resp. Mod.* 8:479–487 (1989)).

As disclosed herein, cytokines such as IL-3, GM-CSF and G-CSF can be useful to radiosensitize a tumor in a subject, and have the additional advantage of stimulating a systemic immune response in the subject. It is well known, however, that administration of a cytokine to a subject is limited by the generalized toxicity induced when the agent is administered systemically. Thus, cytokines may be better administered locally, for example, at the site of a tumor.

A cytokine can be administered by injection as a solution into the site of a tumor. Furthermore, the cytokine can be administered as a cytokine polypeptide, or can be administered in the form of a nucleic acid molecule encoding the cytokine, wherein the nucleic acid molecule is taken up by a cell in the tumor and the cytokine is expressed therefrom. Where a nucleic molecule encoding a cytokine is administered to the site of a tumor, the nucleic acid molecule generally is linked to an appropriate regulatory such as a promotor that provides selective expression of the cytokine at the site of the tumor (see, for example, Seung et al., *Canc. Res.* 55:5561–5565 (1995), which is incorporated herein by reference). In addition, the nucleic acid molecule encoding the cytokine can be linked to a vector such as a retrovirus vector (see below) or the nucleic acid molecule encoding the cytokine can be physically associated with a formulation such as a liposome or an inert particle such as gold.

Preferably, the cytokine is expressed from a cell such as a tumor cell that has been genetically modified, in vitro or in vivo, to express the cytokine. Expression of a cytokine from a genetically modified cell provides the advantage that sustained, localized expression of the cytokine can occur, thus obviating the need for repeated administrations.

Various studies have been performed with tumor cells genetically modified to express a cytokine. As discussed above, for example, tumor cells that were genetically modified to express TNF-$\alpha$ and injected into unmodified tumors growing in immunodeficient mice, sensitized the tumor to radiation therapy more than did the corresponding unmodified tumor cells (Weichselbaum et al., supra, 1994; Hallahan et al., supra, 1995). In addition, human renal carcinoma cells that were genetically modified to express IL-2, Ifn-$\alpha$, or both cytokines, then irradiated with a dose of radiation that inhibited the growth, but not cytokine expression, of the genetically modified cells, lost their tumorigenicity as determined following injection into T cell depleted mice (Belldegrun et al., *J. Natl. Canc. Inst.* 85:207–216 (1993), which is incorporated herein by reference). In addition, the genetically modified renal carcinoma cells prevented the growth of unmodified renal carcinoma cells when injected together, but not if the genetically modified cells were injected at a different site from the unmodified cells (Id.). These studies indicate that tumor cells that are genetically modified to express a cytokine can be used for local delivery of the cytokine to a desired site such as a tumor.

In other studies, intraperitoneal immunization of mice with either immunogenic and non-immunogenic tumor cells, each of which was genetically modified to express IL-3, protected the mice from later challenge with the corresponding unmodified tumor cells (McBride et al., *Folia Biolog.* 40:62–73 (1994), which is incorporated herein by reference; see Example I). These results demonstrate that immunization of IL-3 expressing tumor cells can stimulate a systemic immune response that protects against a later challenge with tumor cells.

As disclosed herein, the expression of a cytokine such as IL-3 or GM-CSF or G-CSF at the site of a tumor can radiosensitize the tumor in a subject and stimulates systemic immunity in the subject against the cancer. For example, a non-immunogenic murine fibrosarcoma tumor cell line, FSAN, or a moderately immunogenic murine fibrosarcoma tumor cell line, FSA (also called FSAR), was genetically modified by transduction using a retroviral vector containing an expressible IL-3 encoding nucleic acid. FSAN cells that were genetically modified to express IL-3 or genetically modified with a vector lacking the IL-3 coding sequence were injected into mice, then, after the tumors attained a size of about 6 to 8 mm, the tumors were irradiated with a single dose of 25 Gray (Gy), 40 Gy or 55 Gy of X-rays (see Example I). In all cases, the IL-3 expressing tumors completely regressed after irradiation, whereas unirradiated IL-3 expressing tumors or irradiated tumor genetically modified with the control vector continued to grow. Furthermore, systemic immunity was stimulated in the cured mice, such that no tumors developed when the mice were subsequently challenged with unmodified tumor cells.

The results of Example I demonstrate that expression of IL-3 at the site of tumor can radiosensitize a tumor and can induce a systemic immune response in the subject against the cancer. In addition, where administration of an immunizing composition is at the site of a tumor, a cytokine such as GM-CSF or G-CSF also can be useful in the present invention. For example, the heterodimeric receptors for IL-3 and GM-CSF share a common chain (Thomson, supra, 1994; see Chaps. 5 and 19), indicating that these cytokines can act, in part, through a shared pathway such as through the stimulation of dendritic cells, which can increase tumor antigen presentation. In addition, G-CSF can induce granulocyte infiltration, as was observed in the IL-3 expressing tumor cells (Example I). Thus, administration of IL-3 or GM-CSF or G-CSF at the site of a tumor can be useful to radiosensitive the tumor and to stimulate a systemic immune response against the cancer.

Where a tumor is radiosensitized by administering IL-3 or GM-CSF or G-CSF at the site of the tumor in a subject, it is not a necessary requirement to include a tumor antigen in the immunizing composition, since the tumor can provide the antigen. However, a cytokine, including an interleukin, interferon, tumor necrosis factor or colony stimulating factor, also can be administered at site other than the tumor site and can induce an immune response that can radiosensitize the tumor in the tumor. In this embodiment of the invention, the immunizing composition also can contain a tumor antigen in addition to the cytokine. If desired, an immunizing composition also can contain an adjuvant such as BCG (see Harlow and Lane, *Antibodies: a laboratory manual* (Cold Spring Harbor Laboratory Press 1988); Mishell and Shiigi, *Selected Methods in Cellular Immunology* (W. H. Freeman and Co. (1980)), each of which is incorporated herein by reference) or other adjuvant as commercially available (Ribi Immunochem Res., Inc.; Hamilton Mont.). As used herein, the term "immunizing composition" is used broadly to mean a cytokine that is in a form for administration to a subject and, in addition, can contain a tumor antigen or other immunostimulatory agent as desired.

When a cytokine is administered at a site other than the tumor site, the cytokine is administered in a form that results in controlled release of desirably low levels of the cytokine. Thus, an immunizing composition can be formulated to contain a cytokine in combination with a material such as DepoFoam™, a wafer, an immunobead, a micropump or other material that provides for controlled slow release of the cytokine. Such controlled release materials are well known in the art and available from commercial sources (Alza Corp., Palo Alto Calif.; Depotech, La Jolla Calif.; see, also, Pardoll, *Ann. Rev. Immunol.* 13:399–415 (1995), which is incorporated herein by reference).

In addition, a cytokine can be administered in combination with a tumor antigen, which can be in the form of a tumor cell, a tumor cell extract or a purified tumor antigen. A tumor antigen can be obtained from the subject or can be a known tumor antigen, including, for example, epithelial cell mucin, which is encoded by the MUC-1 gene, or the melanoma antigen, MZ2-E, which is encoded by the MAGE-1 gene, each of which is associated with particular tumor cells (Finn, *Curr. Opin. Immunol.* 5:701–708 (1993), which is incorporated herein by reference).

An immunizing composition also can comprise a tumor cell, which can be obtained from the subject to be treated, that is genetically modified to express a cytokine. It should be recognized that, while reference is made to the "expression" of a cytokine by a cell, such a cell that is useful in the invention also must secrete the cytokine. The genetic modification of a subject's tumor cells to express a cytokine provides the advantage that, in addition to expression of the cytokine, the tumor cell also presents a tumor antigen, against which an active immune response can be generated.

If a subject's tumor cells are not readily available, another type of cell can be genetically modified to express a cytokine and, in addition, can be genetically modified to express a tumor antigen, which can be the same as the tumor antigen expressed on the subject's cancer cells or can be a known tumor antigen as disclosed above. Such genetically modified cells, which express a tumor antigen and a cytokine, are referred to herein as "carrier" cells (see PCT/US92/08999, filed Oct. 23, 1992, which is incorporated herein by reference).

Genetically modifying a cell to express a known tumor antigen can be particularly useful when the tumor cells to be genetically modified are not obtained from the subject to be treated. For example, it may not be possible to obtain a sufficient number of tumor cells from a cancer patient or the patient's tumor cells may not be adaptable to growth in culture. In this case, cells that do not express a particular tumor antigen that is expressed by the patient's cancer cells can be genetically modified to express the tumor antigen and, in addition, can be genetically modified to express a cytokine. Upon administration of such a genetically modified carrier cell to the subject, the subject's immune response against the cancer can be stimulated and a tumor in the subject can be sensitized to radiation therapy.

A cytokine also can be expressed from a genetically modified cell such as a fibroblast or an antigen presenting cell such as a monocyte, a dendritic cell or a lymphocyte. Such cells, which can be obtained from the subject or can be allogenic cells, are referred to herein as "cytokine-expressing cells" or "CE cells" and can be prepared as disclosed herein or using methods well known in the art (see PCT/US92/08999, supra, 1992). Such CE cells can be administered at the site of a tumor or, if administered at a site other than a tumor site, preferably, are administered in combination with a tumor antigen.

A cell such as a tumor cell that is genetically modified to express a cytokine can be further modified to express an immunostimulatory agent such as the costimulatory B7 molecules, B7.1 and B7.2, (Baskar et al., *Proc. Natl. Acad. Sci., USA* 90:5687–5690 (1993); Townsend and Allison, *Science* 259:368–370 (1993); Tan et al., *J. Immunol.* 149:32217–3224 (1992), each which is incorporated herein by reference), autologous MHC class I and class II molecules (Plautz et al., *Proc. Natl. Acad. Sci., USA* 90:4645–4649 (1993); Hui et al., *Fems Microbiol. Immunol.* 2:215–221 (1990); Ostrand-Rosenberg et al., *J. Immunol.* 144:4068–4071 (1990), each of which is incorporated herein by reference), allogeneic histocompatability antigens such as HLA-B7 (Nabel et al., *Proc. Natl. Acad. Sci., USA* 90:11307–11311 (1993), which is incorporated herein by reference) and known tumor antigens (Finn, supra, 1993). For example, a subject's cancer cell may not express an MHC class I or II molecule and, as a result, would not induce an optimal immune response. In such a case, expression of the appropriate MHC molecule can be useful for stimulating an immune response in the subject against the cancer. Methods for determining whether a tumor cell expresses a particular immunostimulatory agent are known in the art and can be used to determine whether the tumor cell should be genetically modified to express the immunostimulatory agent.

In some aspects of the invention, the administration of viable tumor cells is required. However, administration of viable tumor cells to a subject requires that the tumor cells be inactivated so they do not grow in the subject. Inactivation can be accomplished by any of various methods, including, for example, by irradiation, which is administered at a dose that inhibits the ability of the cells to replicate but does not immediately kill the tumor cells. Where the irradiated tumor cell is a carrier cell that has been genetically modified to express a cytokine, it is known that such irradiation does not substantially affect the expression of the cytokine (Belldegrun et al., supra, 1993). Treatment of tumor cells with a cytostatic agent or with a low dose of a cytotoxic agent also can render the cells reproductively inactive. Such viable tumor cells can present tumor antigens to the subject's immune system but cannot multiply and form new tumors.

It is further recognized that, in some cases, a tumor cell can express an immunosuppressive agent such as a TGFβ. Thus, if it is desirable to use such a tumor cell as an antigen or as a carrier cell in the present invention, the tumor cell can be genetically modified to reduce the expression of the immunosuppressive factor. Tumor cells that produce immunosuppressive factors are known in the art and are present, for example, in carcinomas, sarcomas, gliomas, melanomas, lymphomas and leukemias (Sulitzeanu, *Adv. Canc. Res.* 60:247–267 (1993), which is incorporated herein by reference). Whether a cancer cell is producing an immunosuppressive agent can be readily determined using methods as disclosed herein or otherwise known in the art.

Immunosuppressive agents are known in the art and include, for example, TGFβ, lymphocyte blastogenesis inhibitory factor, the retroviral p15E protein, suppressive E-receptor (see Sulitzeanu, supra, 1993) and extracellular matrix molecules such as fibronectin and tenascin (Olt et al., *Cancer* 70:2137–2142 (1992); Hemasath et al., *J. Immunol.* 152:5199–5207 (1994), each of which is incorporated herein by reference). It is recognized, for example, that various isoforms of TGFβ such as TGFβ1, TGFβ2, TGFβ3, TGFβ4 and TGFβ5 exist (see, for example, Roszman et al., *Immunol. Today,* 12:370–274 (1991); Constam et al., *J. Immunol.,* 148:1404–1410 (1992); Elliot et al., *J. Neuro-Oncology,* 14:1–7 (1992), each of which is incorporated herein by reference) and that the immunosuppressive effect of one or more of these isoforms of TGFβ depends, for example, on the target cell. The term "TGFβ" is used generally herein to mean any isoform of TGFβ, provided the isoform has immunosuppressive activity.

The present invention provides a method of reducing the severity of a cancer in a subject by administering to the subject an immunizing composition, which stimulates an immune response that radiosensitizes a tumor in the subject, then administering a radiotherapeutic dose of radiation to the tumor. As used herein, the term "reducing the severity of a cancer" means that the clinical signs or symptoms of the cancer in a subject are indicative of a beneficial effect to the subject due to treatment using a method of the invention.

Although complete remission is the optimal result, it is recognized that any decrease in the rate of progression of the cancer can provide a palliative effect in the subject, thus improving the subject's quality of life. Methods for determining whether a treatment is reducing the severity of a cancer are well known in the art and include, for example, imaging methods such as magnetic resonance imaging, computerized axial tomography and X-rays, and tumor marker assays such as the detection of levels of circulating carcinoembryonic antigen (CEA) or prostate specific antigen or the like or by detecting the activation of immunoeffector functions in a subject such as the activation of tumor cytolytic immunoeffector cells.

A method of the invention can reduce the severity of a cancer in a subject, by sensitizing a tumor in the subject to radiotherapy. In addition, a method of the invention can provide systemic immunity against the subject's cancer, such that cancer cells that are not killed by the radiotherapy are killed by the subject's immune response. The presence of such an immune response can be identified by comparing the immune functions of a subject prior to administration of an immunizing composition with the immune functions following administration. Such immune functions can be determined using methods well known in the art for measuring a humoral or cellular immune response (see, for example, Harlow and Lane, supra, 1988).

Genetic modification of a tumor cell or a fibroblast or antigen presenting cell for use in the present invention is advantageous because the genetically modified cell provides sustained expression of the cytokine. Viral vectors such as retrovirus, adenovirus or adenovirus-associated vectors can be particularly useful for genetically modifying a cell (see, for example, Flotte, *J. Bioenerg. Biomemb.,* 25:37–42 (1993) and Kirshenbaum et al., *J. Clin. Invest,* 92:381–387 (1993), each of which is incorporated herein by reference; see, also, Hallahan et al., supra, 1995). Such vectors are particularly useful when the vector contains a promoter sequence, which can provide constitutive or, if desired, inducible or tumor selective expression of a cloned nucleic acid sequence. Such vectors are well known in the art (see, for example, *Meth. Enzymol.,* Vol. 185, D. V. Goeddel, ed. (Academic Press, Inc., 1990), which is incorporated herein by reference) and available from commercial sources (Promega, Madison, Wisc.). In particular, a vector containing a radiation inducible promotor can be useful in the present invention (see, for example, Hallahan et al., supra, 1995).

Vectors can be introduced into a cell or into cells within a tumor by any of a variety of methods known in the art (see, for example, Sambrook et al., *Molecular Cloning: A laboratory manual* (Cold Spring Harbor Laboratory Press 1989); and Ausubel et al., *Current Protocols in Molecular Biology*, John Wiley and Sons, Baltimore, Md. (1994), each of which is incorporated herein by reference). Such methods include, for example, transfection, lipofection, electroporation and infection with recombinant vectors or the use of liposomes.

Introduction of nucleic acids by infection (transduction) using a viral vector is particularly advantageous in that it can be effective in vitro or in vivo. Higher efficiency can also be obtained due to the infectious nature of a viral vector. Moreover, viruses are very specialized and typically infect and propagate in specific cell types. Thus, their natural specificity can be used to target the vectors to specific tumor cell types in a biopsy culture, which may be contaminated with other cell types. Viral or non-viral vectors can also be modified with specific receptors or ligands to alter target specificity through receptor mediated events.

A nucleic acid molecule also can be introduced into a cell using methods that do not require the initial introduction of the nucleic acid sequence into a vector. For example, a nucleic acid sequence encoding a cytokine can be introduced into a cell using a cationic liposome preparation (Morishita et al., *J. Clin. Invest.*, 91:2580–2585 (1993), which is incorporated herein by reference; see, also, Nabel et al., supra, 1993)). In addition, a nucleic acid sequence can be introduced into a cell using, for example, adenovirus-polylysine DNA complexes (see, for example, Michael et al., *J. Biol. Chem.*, 268:6866–6869 (1993), which is incorporated herein by reference). Other methods of introducing a nucleic acid sequence are well known (see Goeddel, supra, 1990).

Nucleic acid sequences encoding various cytokines have been cloned and are available for use (GenBank; Thomson, supra, 1994). Nucleic acid sequences encoding, for example, cytokines such as various interleukins, including IL-3, interferons and colony stimulating factors, including GM-CSF and G-CSF, are available from the American Type Culture Collection (see ATCC/NIH Repository Catalogue of Human and Mouse DNA Probes and Libraries, 6th ed., 1992) or are available commercially (Amgen, Thousand Oaks, Calif.; see, also, Patchen et al., *Exptl. Hematol.*, 21:338–344 (1993); Broudy et al., *Blood*, 82:436–444 (1993), each of which is incorporated herein by reference).

Selectable marker genes encoding, for example, a polypeptide conferring neomycin (neo) resistance also are readily available and, when linked to a nucleic acid sequence or incorporated into a vector, allow for the selection of cells that have successfully incorporated the desired nucleic acid sequence. A "suicide" gene also can be incorporated into a vector so as to allow for selective inducible killing of a cell, particularly of a genetically modified tumor cell, when the treatment is completed or otherwise terminated. A gene such as the herpes simplex virus thymidine kinase gene (TK) can be used as a suicide gene to provide a means of inducible destruction of a cell. For example, when a cell such as a tumor cell no longer is useful in the subject, a drug such as acyclovir or gancyclovir can be administered to the subject. Either of these drugs selectively kills cells expressing a viral TK, thus eliminating the genetically modified cells. Additionally, a suicide gene can encode a non-secreted cytotoxic polypeptide and can be linked to an inducible promotor. If destruction of the cells is desired, the appropriate inducer of the promotor is administered so that the cytotoxic polypeptide is expressed.

Numerous methods are available for transferring nucleic acid sequences into cultured cells, including the methods described above. In addition, a useful method can be similar to that employed in previous human gene transfer studies, where tumor infiltrating lymphocytes (TILs) were modified by retroviral gene transduction and administered to cancer subjects (Rosenberg et al., *New Engl. J. Med.* 323:570–578 (1990); see, also, U.S. Pat. No.: 5,460,959, issued Oct. 24, 1995; U.S. Pat. 5,399,346, issued Mar. 21, 1995; each of which is incorporated herein by reference). In the Phase I safety study of retroviral mediated gene transfer, TILs were genetically modified to express the neomycin resistance gene. Following intravenous infusion, polymerase chain reaction analyses consistently found genetically modified cells in the circulation for as long as two months after administration. No infectious retroviruses were identified in these subjects and no side effects due to gene transfer were noted in any subjects. These retroviral vectors have been altered to prevent viral replication by the deletion of viral gag, pol and env genes.

When retroviruses are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. Hence, all retroviral vector supernatants used to infect subject cells will be screened for replication competent virus by standard assays such as PCR and reverse transcriptase assays.

As discussed above, a cancer cell can express an immunosuppressive agent such as an immunosuppressive isoform of TGFβ. Such cancer cells should be genetically modified to reduce or inhibit the expression of the immunosuppressive agent if the cells are to be used as carrier cells or are to be administered in combination with an immunostimulatory agent such as a cytokine, CE cells or the like. Reduction or inhibition of expression of an immunosuppressive agent that is expressed by a tumor cell can be accomplished using known methods of genetic modification. For example, a tumor cell expressing an immunosuppressive agent such as an immunosuppressive isoform of TGFβ can be genetically modified such that the expression of the TGFβ is reduced or inhibited using a homologous recombination gene "knock-out" method (see, for example, Capecchi, *Nature*, 344:105 (1990) and references cited therein; Koller et al., *Science*, 248:1227–1230 (1990); Zijlstra et al., *Nature*, 342:435–438 (1989), each of which is incorporated herein by reference; see, also, Sena and Zarling, *Nat. Genet.*, 3:365–372 (1993), which is incorporated herein by reference). The homologous recombination gene knock-out method provides several advantages. For example, expression of a gene encoding an immunosuppressive agent such as a TGFβ gene in a tumor cell can be inhibited completely if both alleles of the target gene are inactivated. In addition to providing complete inhibition of the immunosuppressive agent, the method of homologous recombination gene knock-out is essentially permanent.

The expression of an immunosuppressive agent by a tumor cell also can be reduced or inhibited by providing in the tumor cell an antisense nucleic acid sequence, which is complementary to a nucleic acid sequence or a portion of a nucleic acid sequence encoding an immunosuppressive agent such as an immunosuppressive isoform of TGFβ. Methods for using an antisense nucleic acid sequence to inhibit the expression of a nucleic acid sequence are known in the art and described, for example, by Godson et al., *J. Biol. Chem.*, 268:11946–11950 (1993), which is incorporated herein by reference. Expression of an immunosuppressive agent by a tumor cell also can be reduced or inhibited by providing in the tumor cell a nucleic acid sequence encoding a ribozyme, which can be designed to recognize and inactivate a specific mRNA such as a mRNA encoding an immunosuppressive isoform of TGFβ (see, for example, McCall et al., *Proc. Natl. Acad. Sci., USA*, 89:5710–5714 (1992); Cremisi et al., *Proc. Natl. Acad. Sci., USA*, 89:1651–1655 (1992); Williams et al., *Proc. Natl. Acad. Sci., USA*, 89:918–921 (1992); Neckers and Whitesell, *Amer. J. Physiol.* 265:L1–12 (1993); Tropsha et al., *J. Mol. Recog.* 5:43–54 (1992), each of which is incorporated herein by reference).

Various assays to determine whether a subject's cancer cells express an immunosuppressive agent such as an immunosuppressive isoform of TGFβ are available and known to those skilled in the art. For example, a radioimmunoassay or enzyme linked immunosorbent assay can be used to detect a specific immunosuppressive agent in a serum or urine sample obtained from a subject. In addition, an assay such as the mink lung epithelial cell assay can be used, for example, to identify TGFβ2 activity (Ogawa and Seyedin, *Meth. Enzymol.* 198:317–327 (1991), which is incorporated herein by reference). A biopsy of the tumor also can be examined, for example, immunohistochemically for the expression of an immunosuppressive agent. In addition, the tumor cells can be evaluated by northern blot analysis, reverse transcriptase-polymerase chain reaction or other known methods (see, for example, Erlich, *PCR Technology: Principles and applications for DNA amplification* (Stockton Press 1989); Sambrook et al., *Molecular Cloning: a laboratory manual* (Cold Spring Harbor Laboratory Press 1989), each of which is incorporated herein by reference).

It is recognized that, in order to sensitize a subject's cancer to radiotherapy, the cytokine must be expressed in an effective amount. As used herein, the term "effective amount" means an amount of a cytokine that can stimulate a systemic immune response in the subject or alter the tumor microenvironment, such that a tumor in the subject is radiosensitized. An effective amount can be determined, for example, by the detecting a stimulation of the subject's immune response or by detecting a reduction in the severity of the subject's cancer following radiotherapy. Such an effective amount can be determined using assays for determining the activity of immunoeffector cells following administration of an immunizing composition to the subject or by monitoring the effectiveness of the radiotherapy using well known imaging methods.

Where an immunizing composition includes a genetically modified cell such as a tumor cell, carrier cell or a CE cell, the number of cells to be administered depends, in part, on the amount of cytokine secreted by the cells. Methods for determining the level of a cytokine expressed by a genetically modified cell are disclosed herein or otherwise known in the art (see, for example, Thomson, supra, 1994; Chap. 25). For example, the IL-3 expressing cells generated as described in Example I produced 50 ng bioactive IL-3 /ml medium/48 hr/$1 \times 10^6$ cells. In general, about $1 \times 10^5$ to about $1 \times 10^7$ cells is required for immunization, depending, for example, on the number of times the composition is to be administered, as well as the amount of a particular cytokine secreted.

Prior to administration, genetically modified cells can be mixed with an appropriate adjuvant or with a pharmacologically acceptable solution such as physiological saline or the like for administration, which can be accomplished by any of various methods such as subcutaneous or intramuscular injection or any manner acceptable for immunization. Pharmacologically acceptable solutions useful for administration to a subject are known in the art (see, for example, Khan et al., supra, 1994; Audibert and Lise, supra, 1993; Mishell and Shiigi, supra, 1980). In addition, various methods of administration can be used and are known to those skilled in the art. Administration can be at a body location other than an active tumor site or, if desired, at the site of a tumor in a cancer subject.

One skilled in the art would know that the effectiveness of therapy can be determined by monitoring a subject's immunoresponsiveness. For example, the cytolytic activity of immune effector cells against the subject's cancer cells can be assayed using well known methods. In addition, the size or growth rate of a tumor can be monitored in vivo using methods of diagnostic imaging.

It is understood that modifications that do not substantially affect the embodiments of this invention also are included within the invention provided herein. Accordingly, the following examples are intended to illustrate but not limit the present invention.

EXAMPLE I

Expression of IL-3 at the Site of a Tumor Radiosensitizes the Tumor

This example demonstrates that a tumor consisting of tumor cells genetically modified to express IL-3 is more radiosensitive than a tumor consisting of unmodified tumor cells.

A. IL-3 Transduction

The Jzen.1 retroviral vector (Laker et al., *Proc. Natl. Acad. Sci., USA* 84:8458–8462 (1987), which is incorporated herein by reference) was used to introduce the full length cDNA encoding murine IL-3 into cultured non-immunogenic (FSAN) or moderately immunogenic (FSA) murine fibrosarcoma cells as previously described (McBride et al., supra, 1992; McBride et al., supra, 1994; see, also, McBride and Howie, *Br. J. Canc.* 53:707–711 (1986), which is incorporated herein by reference).

Briefly, the IL-3 cDNA was inserted downstream of the 5'-LTR promoter and upstream of a neo gene driven by an internal TK promotor present in the vector. The IL-3-containing vector was transfected using calcium phosphate precipitation into the ecotropic packaging cell line GP+env-86 (Markowitz et al., *J. Virol.* 62:1120–1124 (1988), which is incorporated herein by reference). Cloned cell lines produced viral titers in excess of $1 \times 10^6$ pfu/ml.

FSA and FSAN tumor cells were infected with the IL-3-containing vector (Jzen-IL-3) or with the parental vector lacking the IL-3 cDNA insert (Jzen) and infected cells were selected in 0.6 mg G418/ml medium. Sequential daily supernatant infections with the retroviral vectors over 3 days transduced about 50% of the cells.

Expression of IL-3 mRNA by the Jzen-IL-3 transfected cell lines was confirmed by northern blot analysis using the murine IL-3 cDNA as a probe. The IL-3 transduced cells expressed the appropriate 4 kb RNA. In addition, IL-3 protein expression was confirmed by $^3$H-thymidine incorporation into the IL-3-dependent B6SUtA murine mast cell line (McBride et al., supra, 1994). IL-3 transduced cells produced approximately 50 ng bioactive IL-3 /ml medium/ $1 \times 10^6$ cells in a 48 hr period.

B. IL-3 Expressing Tumor Cells are Immunogenic

Subcutaneous injection of $(2.5–3.0) \times 10^3$ FSA or FSAN cells result in 50% incidence of tumors (TD-50) in the C3Hf/Sed/Kam female mice (10–12 weeks old) used in these studies. In comparison, IL-3 transduced FSA (FSA-IL-3) or FSAN (FSAN-IL-3) cells had a TD-50 of $1.2 \times 10^6$ or $2.8 \times 10^5$ cells, respectively. The decreased tumorigenicity is correlated with granulocyte infiltration into the tumors (see McBride et al., supra, 1994). For all experiments described herein, appropriate controls were run in parallel, including the comparison of genetically modified cells with the corresponding unmodified cells or cells modified with the control Jzen.1 vector.

The ability of irradiated IL-3 expressing tumor cells to induce immunity to a subsequent challenge of unmodified tumor cells was examined. Cells were irradiated using a Gammacell 220 (Atomic Energy Limited; Canada) with a cobalt source at a dose rate of 3.3 Gy/min to a total of 30 Gy. $1 \times 10^6$ irradiated (30 Gy) IL-3 transduced FSA (FSA-IL-3) or FSAN (FSAN-IL-3) cells were injected intraperitoneally into mice, then, 10 days later, the mice were challenged with $1 \times 10^6$ unmodified FSA or FSAN cells, respectively. The number of immunizing IL-3 transduced tumor cells was deliberately chosen to be too low to protect against growth of the moderately immunogenic FSA tumor cells in order allow the detection of enhanced immunogenicity.

Immunization with the irradiated IL-3 transduced tumor cells, but not with Jzen.1 modified tumor cells, induced specific immunity against the immunizing cell type (i.e., FSA or FSAN), protecting the mice from subsequent challenge with unmodified tumor cells (McBride et al., supra, 1994). Complete protection occurred in 80% to 90% of the immunized mice and no cross-protection was observed against the antigenically unrelated tumor.

The generation of immunologic memory in the immunized mice was demonstrated by intravenously injecting $2 \times 10^7$ spleen cells from immunized mice or control (not previously treated) mice into syngeneic C3H SCID mice bearing previously established 4 day old parental FSA or FSAN tumors. Regression of the established tumors was observed following adoptive transfer of spleen cells from the immunized mice but not from the control mice. In addition, a moderate amount of cross-protection was observed against the non-immunizing tumor cells (McBride et al., supra, 1994). These results demonstrate that a specific, systemic immune response is induced in mice immunized with IL-3 expressing tumor cells.

C. IL-3 Expressing Tumor Cells are Radiosensitized $(1–5) \times 10^6$ IL-3 transduced FSA or FSAN cells or Jnez.1 transduced FSA or FSAN cells were injected subcutaneously into the thigh muscles of mice (N=5–10). After about 16 to 20 days, when the tumor were about 6 to 8 mm in diameter, the tumors were irradiated. For irradiation, mice were placed in a full body shield, with the tumor bearing thigh exposed. Tumors were irradiated using a 250 kVp Phillip's X-ray source at a dose rate of 11.2 Gy/min. The tumors in mice bearing the moderately immunogenic FSA tumors were irradiated with a single dose of 25 Gy or 40 Gy. The tumors in mice bearing the non-immunogenic FSAN tumors were irradiated with a single dose of 55 Gy.

IL-3 expressing FSA tumors regressed completely following radiotherapy with 25 Gy or 40 Gy. In comparison, unirradiated IL-3 expressing FSA tumors and irradiated unmodified parental FSA tumors continued growing during the course of the experiment, although growth of the irradiated, unmodified FSA tumors was slightly delayed following irradiation. Furthermore, mice that were cured of the IL-3 expressing FSA tumors were protected from challenge with $2 \times 10^6$ unmodified FSA tumor cells, but not of FSAN tumor cells.

Similarly, IL-3 expressing FSAN tumors regressed completely following radiotherapy with 55 Gy, whereas Jzen.1 modified FSAN tumors continued to grow after a brief delay due to the irradiation. In addition, mice cured of the IL-3 expressing FSAN tumors were protected from challenge with unmodified FSAN cells.

These results demonstrate that the expression of IL-3 at the site of tumor radiosensitizes the tumor, thus allowing complete regression of an otherwise progressive tumor. In addition, a specific, systemic immune response was generated such that no tumors formed upon further challenge with tumor cells.

EXAMPLE II

General Considerations for Treatment of a Subject

This example illustrates the general factors to consider in treating a cancer patient with a method of the invention.

Patient Selection

Patients will have a histologically confirmed diagnosis of cancer and can have metastatic lesions. Patients with tumors that must be resected for therapeutic purposes or with tumors readily accessible for biopsy can be treated as disclosed herein. Autologous fibroblasts and tumor cells can be cultured using routine methods. However, where the autologous tumor cells are not amenable to growth in culture, tumor antigens can be provided by sources as disclosed herein. Thus, allogeneic haplotype-matched genetically modified tumor cells can be used provided such tumor cells are of the same histologic origin as the patient's tumor.

Pretreatment Evaluation

Standard pretreatment evaluations are performed as follows:

1) History and physical examination including a description and quantitation of disease activity and tissue-typing of the patient.

2) Performance Status Assessment
   0=Normal, no symptoms
   1=Restricted, but ambulatory
   2=Up greater than 50% of waking hours, capable of self-care
   3=Greater than 50% of waking hours confined to bed or chair, limited self-care
   4=Bedridden 3) Pretreatment laboratory analysis, including complete blood count, including differential count, platelet count, PT, PTT, glucose, BUN, creatinine, electrolytes, SGOT, SGPT, LDH, alkaline phosphatase, bilirubin, uric acid, calcium and total protein albumin.

Other analyses are performed as deemed appropriate, including urinalysis, serum complement levels and immunophenotyping of peripheral blood B cell and T cell subsets. In addition, pretreatment evaluations can include chest X-ray and other diagnostic studies including computerized tomography, magnetic resonance imaging or radionuclide scans to document and quantify the extent of disease activity. Follow-up evaluations of these assessments are performed at regular intervals during the course of therapy (approximately every 1 to 3 months) to monitor the subject's response to therapy and to identify potential signs of toxicity, thus permitting adjustments in the number and distribution of immunizations.

Restrictions on Concurrent Therapy

For optimal effects of this treatment, patients should receive no concurrent therapy which is known to suppress the immune system.

Treatment Protocol

Each patient will receive either intratumoral or subcutaneous administrations an immunizing composition, which can be provided in the form of autologous or allogeneic haplotype-matched carrier cells or in the form of CE cells and a tumor antigen, if desired. Tumor cells generally will be irradiated. Prior to administration, tumor cells can be irradiated with approximately 70 to 100 Gy of radiation, to render the tumor cells incapable of proliferation in vivo.

When an immunizing composition is administered to the site of a tumor, radiotherapy can begin one to three days following the administration. When immunization is at a site other than the tumor, immunization generally will require two to four administrations of the immunizing composition at one to four week intervals, with adjustments being made as required. Radiotherapy can begin concurrently with the immunization protocol, since the localized radiation will not substantially affect the immunoresponsiveness of the subject. Preferably, radiotherapy will begin after it has been determined that the patient's immune response has been stimulated by the immunizations.

Conventional methods of radiotherapy are performed. The stimulation of a patient's immune response will be determined by standard methods, including, for example, detecting the presence of activated immunoeffector cells either in vitro or by detecting a delayed hypersensitivity-type reaction.

In general, a tumor biopsy is taken approximately two months prior to the initiation of the methods disclosed herein. If the tumor cells are adaptable to tissue culture, they can be genetically modified to express a cytokine gene and used as carrier cells. However, even if the tumor cells cannot be grown in culture, they can be stored under appropriate conditions and used as a source of tumor antigen, if desired.

The immunizing composition is administered in a form that provides controlled slow release of the cytokine, particularly when administration is at a site other than the tumor. In addition, if a tumor cell or a carrier cell is not the source of the cytokine, irradiated unmodified tumor cells also can be administered as a source of tumor antigen, particularly when administration is at a site other than the tumor.

Where administration involves, for example, the use of IL-3-expressing cells, the level of IL-3 secreted at the site of immunization can be escalated as required during the immunization procedure. The number of injected IL-3-expressing cells will remain relatively constant at approximately $1 \times 10^5$ to $1 \times 10^7$ cells per administration site by adding an appropriate number of irradiated unmodified cells. Multiple immunization sites can be used if it is deemed desirable to increase the dose of the cytokine to the subject. The subject will be physically examined on each of the three consecutive days following administration and physical and laboratory evaluations will be made at weekly intervals.

Dose Adjustments

The immunoresponsiveness of the subject is determined using the assays described above, including, for example, assays to determine changes in the activity of the cellular immune response in the subject. So long as no toxicity is observed, subsequent administrations are administered at intervals of 1 to 4 weeks, as desired. The results of the cellular and humoral immunoresponsiveness assays and tumor monitoring studies can be used to optimize the treatment protocol as determined by one skilled in the art. Although toxic side effects are not expected to result, potential side effects can be treated using conventional methods.

Treatment of Potential Toxicity

Unacceptable toxic side effects at the site of administration are not expected to result during the course of treatment. However, potential side effects can be treated as required. For example, if massive tumor cell lysis results, any resulting uric acid nephropathy, adult respiratory distress syndrome, disseminated intravascular coagulation or hyperkalemia will be treated using standard methods well known in the art. Local toxicity at the sites of administration will be treated with either topical steroids and, if necessary, surgical excision of the injection site. Generalized hypersensitivity reactions such as "the chills," fever or rash will be treated symptomatically with antipyretics and antihistamines. Patients should not be treated prophylactically. Edema, arthralgia, lymphadenopathy or renal dysfunction can be treated using corticosteroids and/or antihistamines. Anaphylaxis will be treated by standard means such as administration of epinephrine, fluids and steroids.

Other Assays

Provided that sufficient material is available for evaluation, the following assays also are performed. Standard immunofluorescence flow cytometry procedures are useful to evaluate changes in the percentage of T cells, natural killer cells and B cells associated with cytokine gene therapy. Monoclonal antibodies specific for T cells (CD2, CD3, CD4, CD8), natural killer cells (CD16, CD57, CD58) and B cells (CD19, CD20) can be used for these studies.

Briefly, Ficoll-Hypaque purified mononuclear cells are incubated with the primary antibody for 1 hr at room temperature, washed, then incubated with fluorochrome conjugated secondary antibody. The cells are washed, fixed and the percentage of positive cells are determined using a Coulter Epics 4 flow cytometer. Incubation of the cells with isotype-matched control antibody instead of the primary antibody is useful as a negative substitution control.

Standard immunohistological methods employing monoclonal antibodies specific for the hematopoietic cell subsets described above can be used to characterize the immune effector cell infiltrates observed in delayed-type hypersensitivity type skin test biopsy sites. Methods for immunohistological evaluations of fresh frozen cryostat tissue sections are well known in the art.

Although the invention has been described with reference to the above examples, it is understood that various modifications can be made without departing from the spirit of the invention. Accordingly, the invention is limited only by the following claims.

I claim:

1. A method of inhibiting the growth of a tumor in a mammal, comprising (a) administering a tumor cell expressing interleukin-3 to said mammal, wherein expression of interleukin-3 stimulates an immune response against the tumor and wherein said tumor has increased radiation susceptibility, wherein said tumor cell has at least one antigen in common with said tumor; and (b) treating said tumor with radiation, wherein the growth of said tumor is inhibited.

2. A method of inhibiting the growth of a solid tumor in a mammal, comprising (a) administering at or around the site of a solid tumor an expressible nucleic acid molecule encoding interleukin-3, wherein following the administration, said interleukin-3 is expressed and stimulates an immune response against the tumor and wherein said tumor has increased radiation susceptibility; and (b) treating said tumor with radiation, wherein the growth of said tumor is inhibited.

* * * * *